United States Patent
Louis et al.

(10) Patent No.: US 9,060,948 B2
(45) Date of Patent: *Jun. 23, 2015

(54) DERMATOLOGICAL/COSMETIC COMPOSITIONS COMPRISING A RETINOID AND BENZOYL PEROXIDE

(75) Inventors: Fabienne Louis, Villeneuve-loubet (FR); Nathalie Willcox, Saint Vallier de Thiey (FR); Sandrine Segura-Orsoni, Mandelieu (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/110,814

(22) Filed: May 18, 2011

(65) Prior Publication Data

US 2011/0318396 A1  Dec. 29, 2011

Related U.S. Application Data

(63) Continuation of application No. 12/318,938, filed on Jan. 13, 2009, now abandoned, which is a continuation of application No. PCT/EP2007/057091, filed on Jul. 11, 2007.

(60) Provisional application No. 60/832,092, filed on Jul. 21, 2006.

(30) Foreign Application Priority Data

Jul. 13, 2006 (FR) ..................... 06 52967

(51) Int. Cl.
| | |
|---|---|
| A61K 31/327 | (2006.01) |
| A61K 8/368 | (2006.01) |
| A61K 8/04 | (2006.01) |
| A61K 8/26 | (2006.01) |
| A61K 8/38 | (2006.01) |
| A61K 8/67 | (2006.01) |
| A61K 8/73 | (2006.01) |
| A61K 31/203 | (2006.01) |
| A61Q 5/00 | (2006.01) |
| A61Q 7/00 | (2006.01) |
| A61Q 17/04 | (2006.01) |
| A61Q 19/00 | (2006.01) |
| A61Q 19/08 | (2006.01) |

(52) U.S. Cl.
CPC ............ *A61K 8/368* (2013.01); *A61K 8/042* (2013.01); *A61K 8/26* (2013.01); *A61K 8/38* (2013.01); *A61K 8/671* (2013.01); *A61K 8/73* (2013.01); *A61K 8/731* (2013.01); *A61K 31/203* (2013.01); *A61K 31/327* (2013.01); *A61Q 5/008* (2013.01); *A61Q 7/00* (2013.01); *A61Q 17/04* (2013.01); *A61Q 19/00* (2013.01); *A61Q 19/008* (2013.01); *A61Q 19/08* (2013.01)

(58) Field of Classification Search
USPC .................................................. 514/717, 725
See application file for complete search history.

(56) References Cited

U.S. PATENT DOCUMENTS

| | | | | |
|---|---|---|---|---|
| 4,355,028 | A | 10/1982 | Kligman et al. | |
| 8,241,649 | B2 * | 8/2012 | Orsoni et al. | 424/401 |
| 8,568,704 | B2 * | 10/2013 | Mallard et al. | 424/78.03 |
| 2002/0035161 | A1 * | 3/2002 | Segura et al. | 514/772.6 |
| 2003/0170196 | A1 | 9/2003 | Orsoni et al. | |
| 2008/0181963 | A1 | 7/2008 | Orsoni et al. | |

FOREIGN PATENT DOCUMENTS

| | | |
|---|---|---|
| FR | 2 687 312 A1 | 8/1993 |
| FR | 2 833 841 A1 | 6/2003 |
| GB | 2 088 717 A | 6/1982 |
| GB | 2 130 486 A | 6/1984 |
| WO | WO 81/00206 A1 | 2/1981 |
| WO | WO 93/20796 A1 | 10/1993 |
| WO | WO 2007092312 A2 * | 8/2007 |

OTHER PUBLICATIONS

Millikan; "Adapalene: an update on newer comparative studies between the various retinoids"; 2000; International Journal of Dermatology; 39; 784-788.*

Pongjanyakul et al.; "Influence of magnesium aluminium silicate on rhelogical, release and permeation characteristics of diclofenac sodium aqueous gels in vitro"; Apr. 2005; J. Pharm. Pharmacol.; 57(4): 429-34; PubMed abstract; PMID: 15831202.*

Elmore; "Final Report on the Safety Assessment of Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth, . . . "; 2003; International Journal of Toxicology, 22(Suppl. 1):37-102.*

Hercules, "Product Data: Nastrosol® 250 Water Soluable Hydroxyethylcellulose" 2005, Aqualon, Accessed Online Nov. 1, 2010, http://www.in-cosmetics.com/ExhibitorLibrary/108/33015e11.pdf.

(Continued)

*Primary Examiner* — Rei-Tsang Shiao
(74) *Attorney, Agent, or Firm* — Dentons US LLP

(57) ABSTRACT

Dermatological/cosmetic compositions contain, in a physiologically acceptable medium, at least one retinoid, dispersed benzoyl peroxide and a gelling system comprising at least two categories of compounds.

16 Claims, No Drawings

(56) References Cited

OTHER PUBLICATIONS

Martin B. et al. "Chemical Stability of Adapalene and Tretinoin When Combined with Benzoyl Peroxide in Presence and in Absence of Visible Light and ultraviolet Radiation"—*British Journal of Dermatology*, Oct. 1998, pp. 8-11, vol. 139, No. Suppl. 52, British Association of Dermatologists, XP008007635.

Michalun et al., "Milady's Skin Care and Cosmetic Ingredients Dictionary," 1994, p. 175, Milady Publishing Company, Albany, NY, ISBN: 1-56253-125-5.

Hercules, "Product Data: Nastrosol® 250 Water Soluable Hydroxyethylcellulose" 2005, Aqualon, Accessed Online Nov. 1, 2010, http://www.in-cosmetics.com/ExhibitorLibrary/108/33015e11.pdf.

\* cited by examiner

DERMATOLOGICAL/COSMETIC COMPOSITIONS COMPRISING A RETINOID AND BENZOYL PEROXIDE

CROSS-REFERENCE TO EARLIER APPLICATIONS

This application is a continuation of U.S. application Ser. No. 12/318,938, filed Jan. 13, 2009, which is a continuation of PCT/EP 2007/057091, filed Jul. 11, 2007 and designating the United States (published in the English language on Jan. 17, 2008 as WO 2008/006848 A1), which claims benefit under 35 U.S.C. §119(e) of U.S. Provisional Application No. 60/832,092, filed Jul. 21, 2006, and claims foreign priority of FR 0652967, filed Jul. 13, 2006; each hereby expressly incorporated by reference in its entirety and each assigned to the assignee hereof.

BACKGROUND OF THE INVENTION

1. Technical Field of the Invention

The present invention relates to dermatological/cosmetic compositions comprising, formulated into a physiologically acceptable medium, at least one retinoid, dispersed benzoyl peroxide and a gelling system which comprises at least two particular categories of compounds.

2. Description of Background and/or Related and/or Prior Art

The administration of several classes of active principles is a therapeutic tool that is frequently employed, especially for treating dermatological disorders.

Specifically, in the treatment of dermatitis it is known to administer corticosteroids such as, for example hydrocortisone, miconazole or betamethasone valerate, antihistamines (e.g., mizolastine) and/or keratolytic agents such as salicylic acid. Various anti-fungal agents such as allylamine derivatives, triazoles, anti-bacterial or anti-microbial agents such as, for example, antibiotics, quinolones and imidazoles are also conventionally combined in the treatment of dermatological diseases. Peroxides, D vitamins and retinoids are also described for the topical treatment of various pathologies associated with the skin or mucous membranes, in particular acne.

The combination of several local treatments (antibiotics, retinoids, peroxides, zinc) is also employed in dermatology to increase the effectiveness of the active principles and to decrease their toxicity (Cunliffe W. J., *J. Dermatol. Treat.*, 2000, 11 (Suppl. 2), 513-514).

The multiple application of various dermatological products may be quite taxing and demanding for the patient.

The advantage is therefore understood in seeking to obtain a novel treatment that is effective on dermatological conditions, that has a stable composition offering good cosmetic quality, allowing a single application and administration that is pleasant for the patient.

However, the formulation of such a composition poses several problems.

Firstly, the effectiveness of benzoyl peroxide is linked to its decomposition when it is placed in contact with skin. Indeed, it is the oxidizing properties of the free radicals produced during this decomposition that result in the desired effect. Thus, in order to maintain an optimal effectiveness of the benzoyl peroxide, it is important to prevent its decomposition before use, that is to say during storage.

However, benzoyl peroxide is an unstable chemical compound which makes its formulation in finished products difficult.

The solubility and stability of benzoyl peroxide have been studied by Chellquist et al. in ethanol, propylene glycol and various mixtures of polyethylene glycol 400 (PEG 400) and water (Chellquist E. M. and Gorman W. G., *Pharm. Res.*, 1992, Vol. 9: 1341-1346). Benzoyl peroxide proved to be particularly soluble in PEG 400 and ethanol.

This document furthermore specifies that the stability of benzoyl peroxide is strongly influenced by the chemical composition of the formulation and by the storage temperature.

Benzoyl peroxide is extremely reactive and degrades in solution at low temperature due to the instability of its peroxide bond.

The authors thus report that benzoyl peroxide in solution degrades more or less quickly in all the solvents studied, depending on the type of solvent and on its concentration.

The degradation times of benzoyl peroxide in PEG 400 (0.5 mg/g), in ethanol and in propylene glycol are respectively 1.4, 29 and 53 days at 40° C. Such a degradation does not allow the preparation of a product useful for sale.

Furthermore, it is known that benzoyl peroxide is more stable in water and propylene glycol when it is in suspension (i.e., in dispersed form), as it is not degraded after being kept for 90 days in these solvents.

Thus, to limit the problem of rapid instability of benzoyl peroxide in solution, it has proved advantageous to formulate the benzoyl peroxide in dispersed form.

Another difficulty to be overcome for preparing a composition comprising both benzoyl peroxide and a retinoid is that most retinoids are particularly sensitive to natural oxidation, to visible light and to ultraviolet light, and since benzoyl peroxide is a strong oxidizer the chemical compatibility of these compounds in one and the same formulation poses numerous stability problems from a physical and chemical viewpoint.

A study on the stability of two retinoids was carried out by combining two commercial products, one containing a retinoid (tretinoin or adapalene) and the second based on benzoyl peroxide (B. Martin et al., *Br. J. Dermatol.*, (1998) 139, (suppl. 52), 8-11).

The presence of the formulation based on benzoyl peroxide causes a very rapid degradation of the oxidation-sensitive retinoids: it is calculated that 50% of the tretinoin is degraded in 2 hours and 95% in 24 hours. In the composition in which the retinoid is adapalene, no degradation of the adapalene was measured over 24 hours.

This study confirms that the benzoyl peroxide is degraded and degrades the oxidation-sensitive retinoids over time by gradually releasing benzoic acid into the initial products.

On the other hand, no indication was given regarding the physical stability of the two compositions brought together, nor on the therapeutic activity likely to be obtained at the end by combining the two active principles in the same composition.

Nothing would prompt these two active agents to be combined in order to obtain a stable gel-type composition, given that it was commonly known that the presence of benzoyl peroxide chemically and physically destabilized this type of composition.

However, it is clear that the too rapid degradation of benzoyl peroxide and the chemical degradation of the retinoids is undesirable insofar as it impairs the effectiveness of the composition containing them.

Furthermore, a finished product, in particular when it is a pharmaceutical or cosmetic composition, must maintain, throughout its shelf life, precise physicochemical criteria that make it possible to guarantee its pharmaceutical or cosmetic quality respectively. Among these criteria, it is necessary that the rheological properties be retained. They define the behavior and texture of the composition during application, but also the release properties of the active principle [1998 SFSTP Commission Report] and the homogeneity of the product when the active principles are present therein in the dispersed state.

In particular, the formulation of benzoyl peroxide and a retinoid in gel form is advantageous for topical treatments, such as those of acne, as it especially avoids maintaining a greasy feel on the skin.

Another difficulty to be overcome for preparing a composition especially comprising benzoyl peroxide, when it is in gel form, is that the gelling agents are destabilized by the benzoic acid released during the degradation of benzoyl peroxide.

Indeed, the most commonly used thickening agents for formulating these compositions with benzoyl peroxide are acrylic acid polymers (Carbomer).

However, the use of carbomers in aqueous gel-type compositions does not give good results in terms of chemical stability of benzoyl peroxide and in terms of rheological stability. As described by Bollinger (Bollinger, *Journal of Pharmaceutical Science*, 1977, Vol. 5), a loss of 5 to 20% benzoyl peroxide has been observed at the end of 2 months at 40° C. depending on the carbomer neutralizer used. Furthermore, the release of benzoic acid causes the depolymerization of the carbomers, causing a drop in viscosity which may result in phase separation.

This instability of benzoyl peroxide gels impairs their effectiveness and their cosmetic quality.

Therefore, the need remains to provide a physically stable gelled composition comprising benzoyl peroxide and a retinoid. However, nothing among the range of therapies proposed to one skilled in this art would suggest the combination, in the same composition, of benzoyl peroxide and a retinoid and several different gelling agents.

SUMMARY OF THE INVENTION

Nonetheless, novel compositions have now surprisingly been developed satisfying this need, which comprise dispersed, free or encapsulated benzoyl peroxide, at least one retinoid and a gelling system comprising at least two categories of compounds, such compositions having good physical stability, that is to say not having a drop in viscosity over time and at ambient temperature (from 20 to 30° C.), and maintaining good chemical stability of the two active agents (benzoyl peroxide and retinoid). In particular, no degradation of the active agents is observed over time and/or at ambient temperature.

The present invention therefore features compositions, especially pharmaceutical compositions, comprising, formulated into a physiologically acceptable medium:
at least one retinoid;
benzoyl peroxide; and
a gelling system which comprises at least two categories of compounds,
said categories of compounds being selected from among silicates, cellulose gelling agents and polysaccharide gums, with the proviso that when at least two gelling agents are selected from among aluminum/magnesium silicate, xanthan gum and hydroxypropyl cellulose, the gelling system is composed of these two gelling agents, or comprises at least one gelling agent different from these three compounds.

The term "gelling system" means a combination of gelling compounds that gives the composition a sufficient viscosity to maintain the retinoid and the benzoyl peroxide in suspension, even under the influence, in particular, of a pH variation due to the release of benzoic acid by the benzoyl peroxide.

The term "physiologically acceptable medium" means a medium that is compatible with the skin, the mucous membranes and/or the integuments.

DETAILED DESCRIPTION OF BEST MODE AND SPECIFIC/PREFERRED EMBODIMENTS OF THE INVENTION

The compositions according to the invention are preferably in the form of an aqueous gel, which is particularly well suited to the target pathologies.

A gel is a system comprising at least one phase (in general one or two phases), which is thermodynamically stable, resulting from the coagulation of a colloidal solution into a three-dimensional network. More specifically, an aqueous gel corresponds to a composition containing, in an aqueous phase, a visco-elastic mass formed from colloidal suspensions.

More specifically, the gelling system comprises at least two categories of compounds, naturally different and distinct, said categories of compounds being selected from among silicates, cellulose gelling agents and polysaccharide gums.

The term "silicate" is understood in particular to mean clay derivatives, more specifically aluminum and magnesium silicates. The silicates are generally obtained from mineral clays having a crystalline lattice that are dissolved and purified in water to optimize the purity and effectiveness of the product. These compounds are especially marketed by R. T. Vanderbilt under the trademark VEEGUM® (for example: VEEGUM® HV or VEEGUM® K).

The amount of silicate may vary over a wide range and depends in particular on the desired viscosity and on the other gelling agent and/or agents present in the composition. To provide an order of magnitude, the silicate may be present in the composition according to the invention in concentrations from 0.1 to 10%, preferably ranging from 0.1 to 5% by weight relative to the total weight of the composition. Advantageously, the amount is from 0.5 to 2%, even more preferably from 0.8 to 1.8%, such as for example 1%, relative to the total weight of the composition.

The term "cellulose gelling agent" means water-soluble polymers derived from cellulose. These polymers form water-soluble ethers (semi-synthetic cellulose) originating from viscous solutions after dissolving in an aqueous solution. Among the cellulose polymers, especially exemplary are methyl cellulose, ethyl cellulose, hydroxypropylmethyl cellulose, hydroxyethyl cellulose, hydroxylpropyl cellulose, carboxymethyl cellulose and hydroxymethyl cellulose. Preferably hydroxypropylmethyl cellulose or hydroxyethyl cellulose are used. These compounds are especially marketed by Dow Chemical under the trademark METHOCEL® (for example: METHOCEL® E4M) or by Hercules under the trademark NATROSOL® (for example: NATROSOL® 250 HHX).

The amount of cellulose gelling agent may vary over a wide range and in particular depends on the desired viscosity and on the other gelling agent and/or agents present in the composition. To provide an order of magnitude, the cellulose-based gelling agent may be present in the composition according to the invention in amounts from 0.1 to 10%, preferably ranging from 0.1 to 5% by weight relative to the total weight of composition. Advantageously, the amount is from 0.5 to 2%, such as for example 0.5%, 1%, 1.5% or 2% relative to the total weight of the composition.

Polysaccharide gums are complex mixtures of several high-molecular weight polysaccharides obtained by exudation from certain plants. Among the different types of polysaccharide gums, non-limiting examples thereof are gum Arabic, gum tragacanth and xanthan gum, amongst another marketed by CP Kelco under the trademark XANTURAL® (for example: XANTURAL® 180).

The amount of polysaccharide gum may vary over a wide range and depends in particular on the desired viscosity and on the other gelling agent and/or agents present in the composition. To provide an order of magnitude, the polysaccharide gum may be present in the composition according to the invention in amounts from 0.01 to 5%, preferably ranging from 0.05 to 2% by weight relative to the total weight of the composition. Advantageously, the amount is from 0.1 to 0.8% such as, for example, 0.1%, 0.2% or 0.5% relative to the total weight of the composition.

The gelling system may comprise two categories of compounds or three categories of compounds, said categories of compounds being selected from among silicates, cellulose gelling agents and polysaccharide gums.

According to one particular embodiment, the gelling system comprising two categories of compounds comprises at least one cellulose gelling agent (in particular hydroxypropylmethyl cellulose or hydroxyethyl cellulose) in combination with a silicate or a xanthan gum, taking into account the condition indicated above.

According to another particular embodiment, the gelling system comprising two categories of compounds comprises at least one silicate, in combination with a polysaccharide gum, taking into account the condition indicated above.

According to another particular embodiment, the gelling system comprising two categories of compounds comprises at least one polysaccharide gum, in combination with a cellulose gelling agent (in particular hydroxypropylmethyl cellulose or hydroxyethyl cellulose), taking into account the condition indicated above.

The gelling system may also comprise at least one silicate, at least one cellulose gelling agent and at least one polysaccharide gum, taking into account the condition indicated above.

Among the gelling systems having three categories of compounds, especially exemplary is the combination of polysaccharide gum, silicate and a cellulose gelling agent, taking into account the condition indicated above.

According to variants of the invention, the subject compositions may, in addition, comprise an additional gelling agent which may especially be selected from among mixtures of polyacrylamides such as the sodium acryloyldimethyltaurate copolymer/isohexadecane/polysorbate 80 mixture marketed under the trademark SIMULGEL 600 by Seppic, the polyacrylamide/C13-14 isoparaffin/laureth-7 mixture such as, for example, that marketed under the trademark SEPIGEL 305 by Seppic, the family of acrylic polymers coupled to hydrophobic chains such as the PEG-150/decyl/SMDI copolymer marketed under the trademark ACULYN 44 (polycondensate comprising at least, as components, a polyethylene glycol having 150 or 180 moles of ethylene oxide, decyl alcohol and methylenebis(4-cyclohexylisocyanate) (SMDI), at 35% by weight in a mixture of propylene glycol (39%) and water (26%)), the family of modified starches such as the modified potato starch marketed under the trademark STRUCTURE SOLANACE or else mixtures thereof.

The compositions according to the invention contain at least one retinoid. The term "retinoid" means any compound that binds to RAR and/or RXR receptors.

Preferably, the retinoid is a compound selected from among the family of benzonaphthalenic retinoids as described in EP 0 199 636, and especially:
6-(3-methylphenyl)-2-naphthoic acid and its methyl ester;
6-(4-tert-butylphenyl)-2-naphthoic acid and its methyl ester;
6-(3-tert-butylphenyl)-2-naphthoic acid and its methyl ester;
6-(3,4-dimethoxyphenyl)-2-naphthoic acid and its methyl ester;
6-(p-(1-adamantylthio)phenyl)-2-naphthoic acid and its methyl ester;
6-(3-(1-adamantyl)-4-methoxyphenyl)-2-naphthoic acid (adapalene) and its methyl ester;
the methyl ester of 6-[3-(1-adamantyl)-4-tert-butyldimethylsilyloxyphenyl)-2-naphthoic acid;
the methyl ester of 6-[3-(1-adamantyl)-4-hydroxyphenyl)-2-naphthoic acid;
6-[3-(1-adamantyl)-4-hydroxyphenyl)-2-naphthoic acid;
the methyl ester of 6-[3-(1-adamantyl)-4-decyloxyphenyl)-2-naphthoic acid;
6-[3-(1-adamantyl)-4-decyloxyphenyl)-2-naphthoic acid;
the methyl ester of 6-[3-(1-adamantyl)-4-hexyloxyphenyl)-2-naphthoic acid;
6-[3-(1-adamantyl)-4-hexyloxyphenyl)-2-naphthoic acid;
the methyl ester of 6-[3-(1-adamantyl)-4-methoxyphenyl)-4-acetoxy-1-methyl-2-naphthoic acid;
6-[3-(1-adamantyl)-4-methoxyphenyl)-4-hydroxy-1-methyl-2-naphthoic acid;
the methyl ester of 6-[3-(1-adamantyl)-4-methoxyphenyl)-4-hydroxy-1-methyl-2-naphthoic acid;
the methyl ester of 6-[3-(1-adamantyl)-4-methoxyphenyl)-1-methyl-2-naphthoic acid;
6-[3-(1-adamantyl)-4-methoxyphenyl)-1-methyl-2-naphthoic acid;
6-[3-(1-adamantyl)-4-methoxyphenyl)-2-naphthalene methanol;
the ethylamide of 6-[3-(1-adamantyl)-4-methoxyphenyl)-2-naphthoic acid;
the morpholide of 6-[3-(1-adamantyl)-4-methoxyphenyl)-2-naphthoic acid;
the methyl ester of 6-[3-tert-butyl-4-methoxyphenyl)-2-naphthoic acid;
6-[3-tert-butyl-4-methoxyphenyl)-2-naphthoic acid;
the methyl ester of 6-[3-(1,1-dimethyldecyl)-4-methoxyphenyl)-2-naphthoic acid;
6-[3-(1,1-dimethyldecyl)-4-methoxyphenyl)-2-naphthoic acid.

In particular, adapalene and also its salts will be preferred.

The term "adapalene salts" means the salt formed with a pharmaceutically acceptable base, especially mineral bases such as sodium hydroxide, potassium hydroxide and ammonia or organic bases such as lysine, arginine or N-methylglucamine.

The term "adapalene salts" is also understood to mean the salts formed with fatty amines such as dioctylamine and stearylamine.

Other retinoids may be selected from among those described in the following patents or patent applications: U.S. Pat. Nos. 4,666,941, 4,581,380, EP 0 210 929, EP 0 232 199, EP 0 260 162, EP 0 292 348, EP 0 325 540, EP 0 359 621, EP 0 409 728, EP 0 409 740, EP 0 552 282, EP 0 584 191, EP 0 514 264, EP 0 514 269, EP 0 661 260, EP 0 661 258, EP 0 658 553, EP 0 679 628, EP 0 679 631, EP 0 679 630, EP 0 708 100, EP 0 709 382, EP 0 722 928, EP 0 728 739, EP 0 732 328, EP 0 740 937, EP 0 776 885, EP 0 776 881, EP 0 823 903, EP 0 832 057, EP 0 832 081, EP 0 816 352, EP 0 826 657, EP 0 874 626, EP 0 934 295, EP 0 915 823, EP 0 882 033, EP 0 850 909, EP 0 879 814, EP 0 952 974, EP 0 905 118, EP 0 947 496, WO 98/56783, WO 99/10322, WO 99/50239, WO 99/65872.

Of course, the amount of the two active agents, benzoyl peroxide and retinoid, in the composition according to the invention, will depend on the combination selected and therefore particularly on the retinoid in question and on the quality of the desired treatment.

The preferred retinoid concentrations are from 0.0001 to 20% by weight relative to the total weight of the composition.

Benzoyl peroxide could also be used in the free form or else in an encapsulated form in a form adsorbed on, or absorbed in, any porous support.

It could for example be benzoyl peroxide encapsulated in a polymer system made of porous microspheres, such as for example microsponges marketed under the trademark MICROSPONGES P009A Benzoyl Peroxide by Cardinal Healthcare.

To provide an order of magnitude, the compositions according to the invention advantageously comprise from 0.0001 to 20% by weight of benzoyl peroxide and from 0.0001 to 20% by weight of retinoid relative to the total weight of the composition, and preferably, respectively, from 0.025 to 10% by weight of benzoyl peroxide and from 0.001 to 10% by weight of retinoid relative to the total weight of the composition.

For example, in compositions for treating acne, benzoyl peroxide is preferably present at concentrations ranging from 2 to 10% by weight and more particularly from 2.5 to 5% by weight relative to the total weight of the composition. Retinoid is itself present in this type of composition at concentrations generally ranging from 0.05 to 1% by weight relative to the total weight of the composition.

Advantageously, the particle size of the retinoid and of the benzoyl peroxide is such that at least 80% by number of particles, and preferably at least 90% by number of particles, have a diameter of less than 25 µm and at least 99% by number of particles have a diameter of less than 100 µm.

According to the invention, advantageously, the gel containing the benzoyl peroxide and a retinoid comprises at least water and may also comprise a propenetrating agent and/or a wetting liquid surfactant.

The compositions of the invention may contain one or more propenetrating agents in preferable concentrations ranging from 0.01 to 20% to more preferably ranging from 2 to 6% by weight relative to the total weight of the composition. Preferably 2, 4 and 5%.

The propenetrating agents should generally not dissolve the active agents at the percentage employed, should not cause exothermic reactions that damage the benzoyl peroxide, should help in the satisfactory dispersion of the active agents and should have anti-foaming properties. Among the propenetrating agents preferably used, without this list being limiting, are compounds such as propylene glycol, dipropylene glycol, propylene glycol dipelargonate, lauroglycol and ethoxydiglycol.

The particularly preferred propenetrating agent is propylene glycol.

Advantageously, the compositions according to the invention may also contain one or more wetting liquid surfactants in preferable concentrations ranging from 0.01 to 10% to more preferably ranging from 0.1 to 2%. The wetting ability is the tendency of a liquid to spread out over a surface.

Preferably, they are surfactants having a HLB (Hydrophillic Lipophilic Balance) of 7 to 12, or else non-ionic surfactants of polyoxyethylenated and/or polyoxypropylenated copolymer type. They should be liquid so as to easily be incorporated into the composition without it being necessary to heat them, the objective being, amongst other things, to obtain a low-temperature manufacturing method, which in no way limits the present invention.

Among the wetting agents preferably employed, without this list being limiting, are compounds of the family of poloxamers and more particularly Poloxamer 124 and/or Poloxamer 182.

The particularly preferred wetting liquid surfactant is Poloxamer 124.

The composition may comprise, in addition, any additive commonly used in the cosmetic or pharmaceutical field, such as sequestrants, antioxidants, sunscreens, preservatives, fillers, electrolytes, humectants, dyes, common mineral or organic bases or acids, fragrances, essential oils, cosmetic active agents, moisturizers, vitamins, essential fatty acids, sphingolipids, self-tanning compounds such as DHA and skin soothing and protective agents such as allantoin.

Of course, one skilled in this art will take care to select this or these optional additional compounds, and/or their amount, so that the advantageous properties of the composition according to the invention are not, or are not substantially, adversely affected.

These additives may be present in the composition in an amount of 0.001 to 20% by weight relative to the total weight of the composition.

Exemplary are, as examples of sequestering agents, ethylenediamine tetracetic acid (EDTA), and also derivatives or salts thereof, dihydroyethylglycine, citric acid, tartric acid, or mixtures thereof.

Exemplary are, as examples of preservatives, benzalkonium chloride, phenoxyethanol, benzyl alcohol, diazolidinylurea, parabens, or mixtures thereof.

Exemplary are, as examples of humectants, glycerol and sorbitol.

In particular, the present invention also features pharmaceutical or cosmetic compositions for topical application to the skin, integuments or mucous membranes, in the form of an aqueous gel, which comprise, formulated into a physiologically acceptable medium that is compatible with topical application to the skin, integuments or mucous membranes, an active phase comprising (expressed as percentage by weight):

20 to 90% of water;
0 to 10%, preferably 0 to 2%, especially 0 to 0.5% of wetting liquid surfactant;
0 to 20%, preferably 0 to 10%, especially 2 to 5% of propenetrating agent;
0.0001 to 20%, preferably 0.025 to 10% of benzoyl peroxide;
0.0001 to 20%, preferably 0.001 to 10% of retinoid; and
0.11 to 25% of a gelling system as described above.

The aqueous phase of the composition according to the invention may comprise water, a floral water such as cornflower water, or a spring or natural mineral water, for example selected from among water from Vittel, waters from the Vichy basin, water from Uriage, water from la Roche Posay, water from la Bourboule, water from Enghien-les-Bains, water from Saint Gervais-les-Bains, water from Néris-les-Bains, water from Allevard-les-Bains, water from Digne, water from Maizières, water from Neyrac-les-Bains, water from Lons-le-Saunier, water from Bonnes, water from Rochefort, water from Saint Christau, water from Furnades and water from Tercis-les-Bains, water from Avène or water from Aix les Bains.

Said aqueous phase may be present in an amount from 10 to 90% by weight relative to the total weight of the composition, preferably from 20 to 85% by weight.

A preferred composition according to the invention comprises, in water:

2.5% of benzoyl peroxide;
0.1% of adapalene;
0.1% of disodium EDTA;
2%-4% of glycerol;
2%-6%; (preferably 2%, 4% or 5%) of propylene glycol
0%-0.05% of sodium docusate;
2%-4% of a gelling system as described above; and
0.2%-0.5% of Poloxamer 124.

A particularly preferred composition according to the invention comprises, in water:

| | |
|---|---|
| Adapalene | 0.1% |
| Benzoyl peroxide | qs 2.5% BPO |
| Propylene glycol | 4% |
| Poloxamer 124 | 0.1% |
| Aluminum/magnesium silicate | 2% |
| Hydroxyethyl cellulose | 1.5% |
| Xanthan gum | 0.5% |
| Glycerol | 2% |
| Sodium docusate | 0.05% |

The methods for preparing the compositions according to the invention are conventional methods that can be carried out by one skilled in this art.

The present invention also features the composition as described previously as medication.

This invention also features the use of the composition as described previously in cosmetics or in dermatology.

On account of the keratolytic, bactericidal and anti-inflammatory activity of benzoyl peroxide and the pronounced activity of retinoids in the fields of cell differentiation and proliferation, the compositions of the invention are particularly suitable in the following therapeutic fields:

1) for treating dermatological conditions or afflictions associated with a keratinization disorder relating to differentiation and proliferation, especially for treating acne vulgaris and comedonal, polymorphous and rosacea acnes, nodulo-cystic acne and acne conglobara, senile acne, secondary acne such as solar, drug or occupational acne and hidradenitis suppurativa;

2) for treating other types of keratinization disorders, especially ichthyosis, ichthyosiform states, Darrier's disease, palmoplantar keratoderma, leukoplakia or leucoplakiform states, and cutaneous or mucous (buccal) lichen;

3) for treating other dermatological conditions or afflictions associated with a keratinization disorder having an inflammatory and/or immuno-allergic component and especially all forms of psoriasis whether they are cutaneous, mucous or ungula, and even psoriatic rheumatism, or else cutaneous atopy, such as eczema or respiratory atopy or else gingival hypertrophy; the compounds may also be used in certain inflammatory conditions that do not exhibit keratinization disorders, such as folliculitis;

4) for treating all dermal or epidermal proliferations, whether benign or malignant, whether or not they are of viral origin, such as verrucas, plane warts, molluscum contagiosum and epidermodysplasia verruciformis, oral or floride papillomatoses and proliferations which may be induced by ultraviolet light especially in the case of actinic keratoses;

5) for repairing or combating skin aging, whether light-induced or chronological, or for reducing pigmentation, or any pathologies associated with chronological and actinic aging;

6) for treating wound-healing disorders or skin ulcers in a preventative or curative manner, for preventing or repairing striae atrophicae, or else for promoting wound healing;

7) for combating sebaceous gland disorders such as hyper-seborrhea of acne or simple seborrhea;

8) in treating any skin condition or affliction of fungal origin, such as tinea pedis and tinea versicolor;

9) in the treatment of dermatological conditions or afflictions having an immunological component;

10) in the treatment of skin disorders due to exposure to UV radiation; and 11) in the treatment of dermatological conditions or afflictions associated with an inflammation or infection of the tissues surrounding the hair follicle, especially due to a microbial colonization or infection, especially impetigo, seborrheic dermatitis, folliculitis, sycosis barbae or those involving any other bacterial or fungal agent.

The compositions according to the invention are particularly useful for the treatment, in a preventative and/or curative manner, of acne vulgaris.

The present invention also features the production of a pharmaceutical preparation useful for preventing and/or treating dermatological conditions linked to cell differentiation and/or proliferation disorders and/or keratinization disorders, more particularly for the production of a pharmaceutical preparation useful to prevent and/or treat acne vulgaris.

The compositions according to the invention also find an application in body and hair hygiene.

The compositions according to the invention particularly find an application in the cosmetics field, in particular for treating acne-prone skin, for hair regrowth, for preventing hair loss, for combating the greasy appearance of the skin or hair, in protecting against the damaging effects of the sun or in treating physiologically greasy skin, or for preventing and/or combating light-induced or chronological aging.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Duos of Gelling Agents a) Silicate/Gum Tragacanth:

| | |
|---|---|
| Water | qs 100% |
| Adapalene | 0.1% |
| Benzoyl peroxide | qs 2.5% BPO |
| Propylene glycol | 2% |
| Poloxamer 124 | 0.2% |
| Disodium EDTA | 0.1% |
| Silicate (Veegum K) | 2% |
| Gum tragacanth | 0.5% |
| Glycerol | 2% |
| Sodium docusate | 0.05% | b) Xanthan Gum/Cellulose (Hydroxyethyl Cellulose):

| | |
|---|---|
| Water | qs 100% |
| Adapalene | 0.1% |
| Benzoyl peroxide | qs 2.5% BPO |

-continued

| | |
|---|---|
| Propylene glycol | 4% |
| Poloxamer 124 | 0.2% |
| Disodium EDTA | 0.1% |
| Hydroxyethyl cellulose (Natrosol HHX) | 2% |
| Xanthan gum (Xantural 18) | 0.2% |
| Glycerol | 4% | c) Cellulose/Silicate:

| | |
|---|---|
| Water | qs 100% |
| Adapalene | 0.1% |
| Benzoyl peroxide | qs 2.5% BPO |
| Dipropylene glycol | 4% |
| Poloxamer 124 | 0.2% |
| Disodium EDTA | 0.1% |
| Hydroxyethyl cellulose (Natrosol HHX) | 2% |
| Silicate (Veegum HV) | 1% |
| Glycerol | 4% |
| Sodium docusate | 0.05% |

Example 2

Trios of Gelling Agents a) Silicate/Cellulose/Xanthan Gum:

| | |
|---|---|
| Water | qs 100% |
| Adapalene | 0.1% |
| Benzoyl peroxide | qs 2.5% BPO |
| Propylene glycol | 4% |
| Poloxamer 124 | 0.2% |
| Disodium EDTA | 0.1% |
| Veegum K | 2% |
| Hydroxyethyl cellulose (Natrosol HHX) | 1.5% |
| Xanthan gum (Xantural 180) | 0.5% |
| Glycerol microsponges | 4% |
| Glycerol | 2% |
| Sodium docusate | 0.05% |

Specifications at T0:

Macroscopic appearance: White, smooth and shiny product

Microscopic appearance: Good dispersion of both active agents.

Physical Stability

| Stability conditions | Time | | |
|---|---|---|---|
| | T 1 month | T 2 months | T 3 months |
| TA | Conforms to specifications | Conforms to specifications | Conforms to specifications |
| 40° C. | Conforms to specifications | Conforms to specifications Slightly yellowing of the product | Conforms to specifications Slightly yellowing of the product |

Chemical Stability:

Adapalene:

Assay of the active by internal calibration in HPLC.

At the starting time (T0) the composition is considered to contain 100% of adapalene. Concentration of adapalene measured in % relative to T0:

| Stability conditions | Time | | | |
|---|---|---|---|---|
| | T 0 | T 1 month | T 2 months | T 3 months |
| AT | NR | NR | NR | 97.7% |
| 40° C. | | NR | NR | NR |

Benzoyl Peroxide:

Assay of the active by internal calibration in HPLC.

At the starting time (T0) the composition is considered to contain 100% of benzoyl peroxide. Concentration of benzoyl peroxide measured in % relative to T0:

| Stability conditions | Time | | | |
|---|---|---|---|---|
| | T 0 | T 1 month | T 2 months | T 3 months |
| AT | 99.2 | NR | NR | 94.8 |
| 40° C. | | 96.3 | 81.6% | 88.7 | b) Silicate/Cellulose/Xanthan Gum:

| | |
|---|---|
| Water | qs 100% |
| Adapalene | 0.1% |
| Benzoyl peroxide | qs 2.5% BPO |
| Propylene glycol | 5% |
| Poloxamer 124 | 0.5% |
| Disodium EDTA | 0.1% |
| Veegum K | 2% |
| Hydroxyethyl cellulose (Methocel E4M) | 0.5% |
| Xanthan gum (Xantural 180) | 0.1% |
| Glycerol | 4% |
| Sodium docusate | 0.05% | c) Silicate/Cellulose/Gum Arabic:

| | |
|---|---|
| Water | qs 100% |
| Adapalene | 0.1% |
| Benzoyl peroxide | qs 2.5% BPO |
| Propylene glycol | 5% |
| Poloxamer 124 | 0.5% |
| Disodium EDTA | 0.1% |
| Veegum K | 2% |
| Carboxymethyl cellulose | 0.5% |
| Gum arabic | 0.1% |
| Glycerol | 4% |
| Sodium docusate | 0.05% |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dermatological/cosmetic composition comprising, in water:
   adapalene;
   benzoyl peroxide;
   a gelling system which comprises aluminum/magnesium silicate, hydroxyethyl cellulose, and xanthan gum;
   a propenetrating agent; and
   a wetting liquid surfactant.

2. A dermatological/cosmetic composition comprising, in water:
   adapalene;
   benzoyl peroxide;
   a gelling system which comprises aluminum/magnesium silicate, hydroxyethyl cellulose and xanthan gum;
   propylene glycol; and
   poloxamer.

3. The dermatological/cosmetic composition as defined by claim 1, which further comprises one or more additives selected from the group consisting of sequestrants, antioxidants, sunscreens, preservatives, fillers, electrolytes, humectants, dyes, common mineral bases, common mineral acids, common organic bases, common organic acids, fragrances, essential oils, moisturizers, vitamins, essential fatty acids, sphingolipids, self-tanning compounds, skin soothing and protective agents.

4. The dermatological/cosmetic composition as defined by claim 2, which further comprises disodium EDTA, glycerol and sodium docusate.

5. The dermatological/cosmetic composition of claim 1, wherein the propenetrating agent is propylene glycol.

6. The dermatological/cosmetic composition of claim 1, wherein the wetting liquid surfactant is poloxamer.

7. The dermatological/cosmetic composition of claim 6, wherein the poloxamer is Poloxamer 124.

8. The dermatological/cosmetic composition of claim 2, wherein the composition comprises:
   0.05% to 1% by weight of adapalene;
   2.5% by weight of benzoyl peroxide; and
   2% to 4% by weight of the gelling system;
   relative to the total weight of the composition.

9. The dermatological/cosmetic composition of claim 8, wherein the composition comprises 0.1% by weight of adapalene, relative to the total weight of the composition.

10. The dermatological/cosmetic composition of claim 8, wherein the gelling system comprises:
    2.0% by weight of aluminum/magnesium silicate;
    1.5% by weight of hydroxyethyl cellulose; and
    0.5% by weight of xanthan gum;
    relative to the total weight of the composition.

11. The dermatological/cosmetic composition of claim 8, wherein the gelling system comprises:
    2.0% by weight of aluminum/magnesium silicate;
    0.5% by weight of hydroxyethyl cellulose; and
    0.1% by weight of xanthan gum;
    relative to the total weight of the composition.

12. The dermatological/cosmetic composition of claim 8, wherein the composition comprises:
    2% to 6% by weight of propylene glycol; and
    0.2% to 0.5% by weight of poloxamer;
    relative to the total weight of the composition.

13. The dermatological/cosmetic composition of claim 12, wherein the composition comprises:
    4% by weight of propylene glycol; and
    0.2% by weight of poloxamer;
    relative to the total weight of the composition.

14. The dermatological/cosmetic composition of claim 13, wherein the poloxamer is Poloxamer 124.

15. The dermatological/cosmetic composition of claim 2, wherein the composition comprises:
    0.05% to 1% by weight of adapalene;
    2.5% by weight of benzoyl peroxide;
    2.0% by weight of aluminum/magnesium silicate;
    1.5% by weight of hydroxyethyl cellulose;
    0.5% by weight of xanthan gum;
    4% by weight of propylene glycol; and
    0.2% by weight of poloxamer;
    relative to the total weight of the composition.

16. The dermatological/cosmetic composition of claim 15, wherein the composition comprises 0.1% by weight of adapalene, relative to the total weight of the composition.

* * * * *